(12) United States Patent
Novich

(10) Patent No.: US 6,274,164 B1
(45) Date of Patent: Aug. 14, 2001

(54) GLASS FIBER CHEMICAL DELIVERY SYSTEM

(75) Inventor: Bruce E. Novich, Pittsburgh, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 0 days.

(21) Appl. No.: 09/662,571

(22) Filed: Sep. 15, 2000

Related U.S. Application Data

(62) Division of application No. 08/994,616, filed on Dec. 19, 1997, now Pat. No. 6,210,703.
(51) Int. Cl.⁷ .............................. A61L 15/00; A61L 15/16
(52) U.S. Cl. ..................... 424/443; 424/444; 424/445; 424/446; 424/447; 424/449
(58) Field of Search .............................. 424/443–7, 449; 435/174, 176; 428/375, 391, 392, 447; 524/26, 28, 588

(56) References Cited

U.S. PATENT DOCUMENTS 5,470,585 * 11/1995 Gilchrist .............................. 424/604

* cited by examiner

Primary Examiner—Shelley A. Dodson
(74) Attorney, Agent, or Firm—Andrew C. Siminerio

(57) ABSTRACT

A glass fiber chemical delivery system including water soluble fiberglass particles containing a chemical composition. The water soluble fiberglass particles may define pores in which the chemical composition is contained or the water soluble fiberglass particles may each define a hollow core containing the chemical composition. As the fiberglass particles dissolve in an aqueous environment, such as within cells of a blood vessel wall or in a reaction vessel, the chemical composition is released.

18 Claims, 2 Drawing Sheets

GLASS FIBER CHEMICAL DELIVERY SYSTEM

This is a divisional of U.S. Patent application Ser. No. 08/994,616, filed Dec. 19, 1997. Now U.S. Pat. No. 6,210, 703.

BACKGROUND OF THE INVENTION

1. Field of the Invention

The present invention relates to glass fiber chemical delivery systems, more particularly, to a glass particulate coated intravascular sent.

2. Prior Art

In patients suffering from certain cardiovascular diseases which cause formation of atherosclerotic plaques within blood vessels, balloon angioplasty has been somewhat successful in reopening blood vessels blocked by such plaques. In order to prevent the blood vessels from recollapsing following balloon angioplasty, it is common for a sent to be inserted into the blood vessel to act as a brace against the inner wall of the blood vessel. Typically, the sent is an expandable stainless steel mesh in which a balloon is disposed. The sent and balloon assembly is inserted into the blood vessel of the patient with a catheter. The balloon is inflated causing the sent to assume a substantially cylindrical shape and engage the walls of the blood vessel. The catheter and balloon are then withdrawn from the blood vessel and the sent remains in position to maintain the blood vessel in an open state. However, it has been found that nearly 70% of patients having intravascular stents experience restinosis in the location of the sent. The sent itself apparently is an irritant to the cells of the blood vessel wall thus stimulating plaque to reform to an even greater degree than the original blockage caused by the first treated plaque.

One solution to this problem of restinosis is to deliver a drug to the blood vessel wall which inhibits or prevents the cells of the blood vessel wall from producing plaque. In particular, certain genes have been identified which will transfect the cells of the blood vessel wall and prevent the cells from producing plaque. Such gene therapy is gaining acceptance in the treatment of cardiovascular disease; however, the delivery of a gene to a specific location within a blood vessel wall remains problematic. Moreover, such a gene or other drug delivered to the location of an intravascular sent should provide sustained relief from the formation of plaque.

Accordingly, a need remains for an intravascular sent which inhibits or prevents restinosis and for a sustained release chemical delivery system which is compatible with a biological environment or other environments.

SUMMARY OF THE INVENTION

These needs are met by the carrier composition for release of a substance and the intravascular drug delivery device of the present invention. The carrier composition includes a plurality of water soluble glass fibers. The fibers are adapted to releasably contain the substance such that the substance is released from the fibers when the fibers are dissolved in water. The fibers preferably have diameters of about four microns to five hundred microns and lengths of about twenty microns to one half inch. The glass fibers may each define a hollow core, wherein the fibers are adapted to releasably contain the substance within the hollow core. Alternatively, the glass fibers may each define at least one pore and wherein the fibers are adapted to releasably contain the substance within the pores. Suitable substances which may be contained within the glass fibers include drugs, fertilizers, biocides, chemical reactants or catalysts. In particular, a drug containing a gene may be contained within the glass fibers.

The present invention further includes a vascular drug delivery including an intravascular sent, preferably an expandable metal mesh, and a water soluble glass composition coated on the sent, wherein the glass composition includes a plurality of water soluble glass fibers and wherein the fibers releasably contain a chemical composition such as a drug. The fibers may be hollow, wherein the chemical composition is releasably contained with the core of the hollow fibers, or the fibers may be porous, wherein the chemical composition is releasably contained in the pores of the porous fibers. The fibers are preferably fixed to the sent via a layer of adhesive disposed therebetween.

The present invention further includes a method of drug delivery having the steps of providing a sustained release drug delivery system, the system including a plurality of water soluble glass fibers and a drug releasably contained within the fibers, administering said system to a human or animal and allowing the fibers to dissolve in water in the human or animal such that the drug is released from within the fibers. The system may be administered orally or parenterally, and preferably is delivered intravenously. In one embodiment, the system includes an intravascular sent, and the fibers are coated on the sent. The glass coated sent is inserted into a blood vessel of the human or animal and, as the glass dissolves, the drug is delivered to cells of a wall of the blood vessel.

The present invention also includes a method of preventing restinosis at a location of an intravascular sent having the steps of providing an intravascular sent, coating the sent with a plurality of water soluble glass fibers containing a drug adapted to prevent restinosis induced by the sent, inserting the coated sent into a blood vessel and allowing the glass fibers to dissolve in water within the blood vessel so that the fibers release the drug. Preferably, the sent bearing the drug filled glass fibers is expanded so that the fibers engage with a wall of the blood vessel and the drug is released into cells of the wall of the blood vessel. The drug may include a gene, and the drug may be releasably contained within pores in the fibers or in a central core of each of the fibers.

The fiberglass sustained release carrier composition of the present invention may be prepared by performing the steps of providing a water soluble glass composition, forming fibers of water soluble glass from the glass composition, creating pores in the fibers to produce porous water soluble fiberglass and grinding the porous water soluble fiberglass to produce ground porous water soluble fiberglass particles. The pores are preferably produced in the water soluble glass composition by reacting the glass with an acid to leach ions out from the glass composition. The substance to be released over time from the carrier composition is mixed with the ground porous water soluble fiberglass particles so that the substance enters the pores. Alternatively, the water soluble glass may be drawn through an annulus to form fibers having hollow cores. The hollow fibers are ground in a similar manner to the porous fibers and subsequently mixed with the substance to be released from the carrier composition so that the substance enters the hollow cores.

A complete understanding of the invention will be obtained from the following description when taken in connection with the accompanying drawing figures wherein like reference characters identify like parts throughout.

DESCRIPTION OF THE PREFERRED EMBODIMENTS

Figure 1:
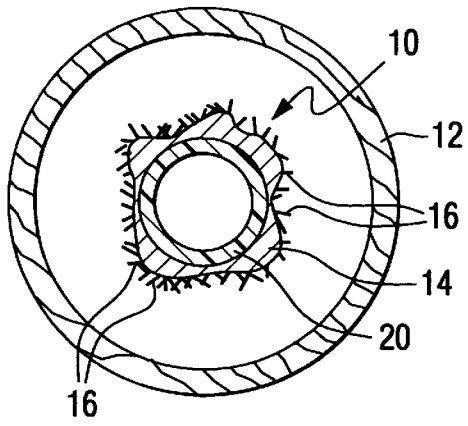
FIG. 1 is a cross sectional view of a blood vessel containing a glass coated sent according to the present invention.
Figure 2:
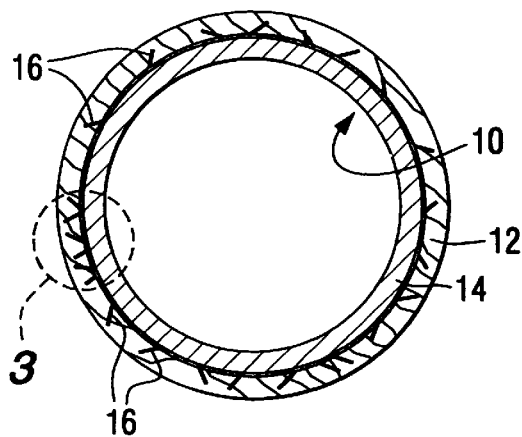
FIG. 2 is a cross sectional view of the blood vessel of FIG. 1 wherein the sent is expanded to engage with the blood vessel wall.
Figure 3:
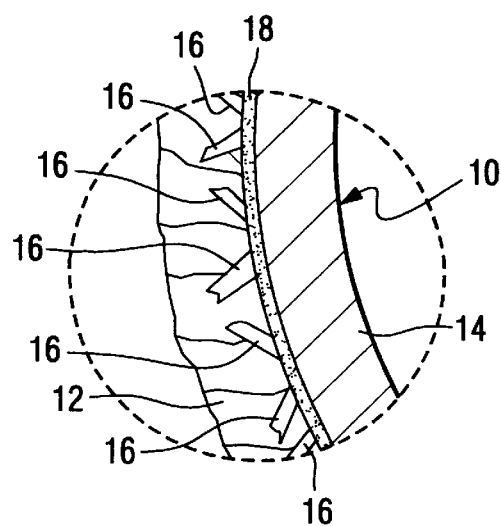
FIG. 3 is an enlarged view of a section of the blood vessel wall and sent depicted in FIG. 2.

The vascular drug delivery device 10 of the present invention is illustrated in FIGS. 1–3 and is configured for use adjacent an inner surface of a wall 12 of a blood vessel. The vascular drug delivery device 10 includes a sent 14 coated with a plurality of water soluble fiberglass particles 16. A conventional intravascular sent includes an expandable mesh formed into a conduit and made of stainless steel or other biocompatible material. When expanded, the sent acquires a substantially cylindrical shape. Suitable stents are available from Guidant, Inc. of Santa Clara, Calif. and Cordis Corporation of Hialeah, Fla. Preferably, the fiberglass particles are fixed to the sent by disposing a layer 18 of a biocompatible adhesive between the sent 14 and fiberglass particles 16. A suitable adhesive may include polyvinylalcohol (PVA), starch, methylcellulose or other gel-like materials known in the art. By the term biocompatible, it is meant that the material may be introduced into the human body without inducing an irritating or other detrimental response thereto. An expandable balloon 20 is disposed within the sent 14. As shown generally in FIG. 2 and in detail in FIG. 3, when the balloon 20 is inflated, the sent 14 expands into a substantially cylindrical shape and urges the fiberglass particles 16 into engagement with the blood vessel wall 12.

The fiberglass particles 16 are formed from a water soluble glass composition. By the phrase water soluble, it is meant that the glass composition dissolves in water or an aqueous environment such as in bodily fluids, including blood.

A portion of each of the fiberglass particles 16 contains a substance which may be a chemical composition such as an anti-restinosis drug composition. By the term drug, it is meant a conventional pharmaceutical or a gene or other substance which may be delivered to the blood vessel wall 12. By the phrase anti-restinosis drug, it is meant a substance which when delivered to the blood vessel wall 12 inhibits or prevents restinosis in the location of the sent 14. A benefit of using a gene is that when the gene enters cells of the blood vessel wall 12, and the cells are transfected, those cells are substantially permanently altered. Alteration of the genetic code of the cells of the blood vessel wall 12 ensures that the cells will no longer produce plaque.

Figure 4A:
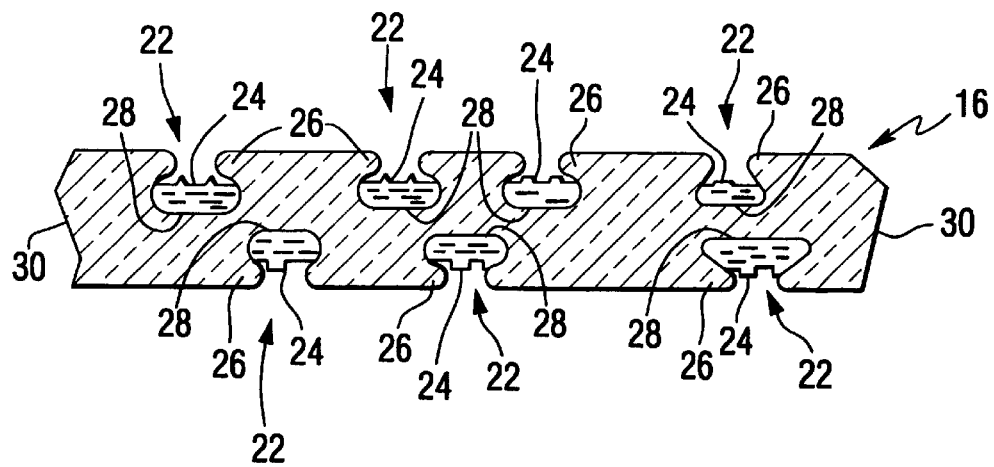
FIG. 4A is a longitudinal cross sectional view of a glass particle according to the present invention.

As depicted in FIG. 4A, the fiberglass particles 16 each define a plurality of pores 22 containing a chemical composition 24. The pores 22 are each preferably ink bottle shaped. In particular, each of the pores 22 has an opening defined by an annular shoulder 26, a diameter of the opening being smaller than a diameter of a base 28 of the pore 22. This ink bottle shape of the pores 22 allows the pores 22 to be easily filled, yet prevents premature escape of the chemical composition 24 out of the pores 22. Opposing ends 30 of the water soluble fiberglass particle 16 are conchoidally shaped; namely, the ends 30 have jagged, rough or uneven surfaces which are particularly suited for engaging the blood vessel wall 12.

Figure 4B:
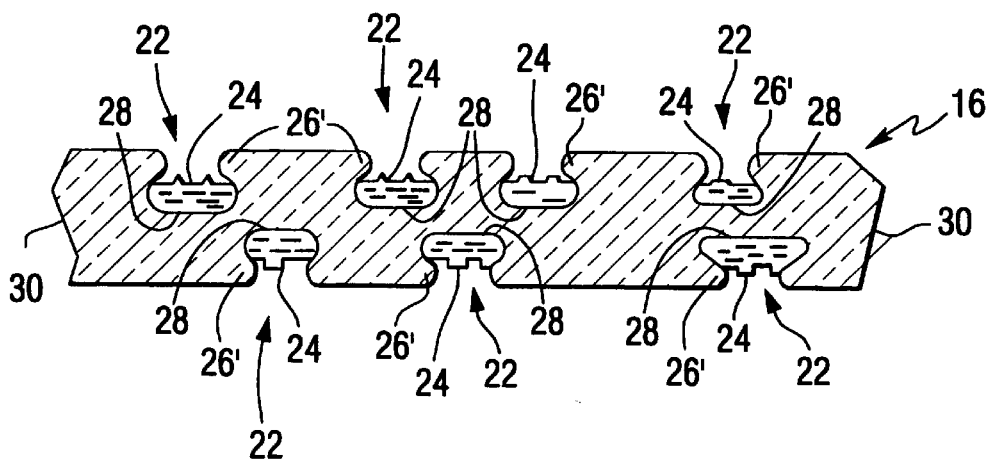
FIG. 4B is a longitudinal cross sectional view of the glass particle depicted in FIG. 4A after dissolution of a portion of the particle.

When the water soluble fiberglass particles 16 are placed in an aqueous environment, the water soluble glass dissolves thus releasing the chemical composition 24. In the fiberglass particle 16, it is believed that as the shoulders 26 of the pores 22 dissolve, the diameter of the opening defined by the shoulders 26 widens allowing the chemical composition 24 to be released from the pores 22. A widened pore 22' is depicted in FIG. 4B. Ultimately, the fiberglass particles 16 may completely dissolve and all the chemical composition 24 contained within the pores 22 of the fiberglass particles 16 will be released to the aqueous environment of the cells of the blood vessel wall 12. The chemical composition 24 will continue to be released from the fiberglass particles 16 until the pores 22 are emptied and/or the shoulders 26 are dissolved away. This mechanism is believed to constitute sustained release of the chemical composition 24 because the delivery rate from the fiberglass particles 16 is determined by the external environment into which the chemical composition 24 is released. The rate at which the shoulders 26 of the pores 22 dissolve is determined in part by the water solubility of the glass of the fiberglass particles 16. Fiberglass particles 16 made from glass having a relatively high water solubility will dissolve more rapidly and release the chemical composition 24 more rapidly than will otherwise similar fiberglass particles 16 made from glass having a relatively low water solubility. Accordingly, the delivery rate of the chemical composition 24 may be controlled by adjusting the water solubility of the glass.

Figure 5:
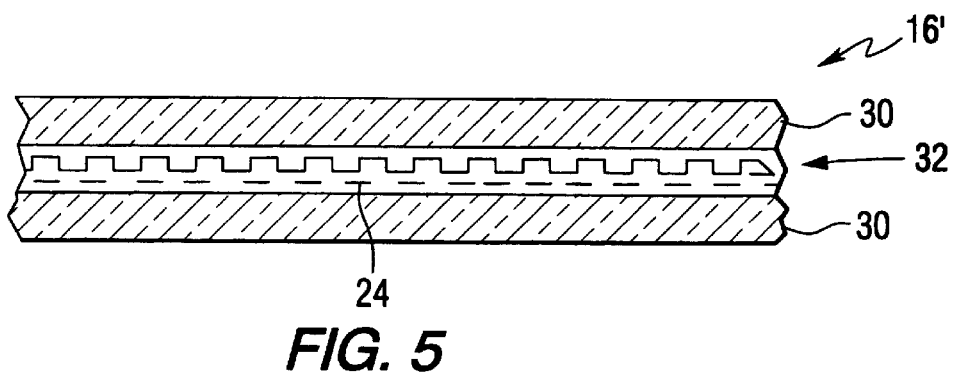
FIG. 5 is a longitudinal cross sectional view of another glass particle according to the present invention.

A modified water soluble fiberglass particle 16' is depicted in FIG. 5. The fiberglass particle 16' defines a hollow core 32 which contains the chemical composition 24. In the hollow fiberglass particle 16', the water soluble glass dissolves over time to shorten the length of the particle 16', thus releasing the drug from the ends 30 of the particle 16'. The modified water soluble fiberglass particles 16' may be used for sustained release of the chemical composition 24 in a manner similar to the particles 16, hence, all references to the particles 16 are applicable to the particles 16' unless stated otherwise.

The adhesive layer 18 used to fix the fiberglass particles 16 to the sent 14 may be water soluble or water insoluble. In certain circumstances, it may be desirable to completely release the fiberglass particles 16 from the sent 14 and, in other circumstances, it may be beneficial to retain the fiberglass particles 16 on the sent 14 until all of the chemical composition 24 has been released. In either circumstance, the fiberglass particles 16 will dissolve over time and the resulting aqueous glass solution will eventually be flushed from the body.

The present invention further includes a method of producing the water soluble fiberglass particles. According to the inventive method, the fiberglass particles 16 are formed by first producing a water soluble glass composition and forming filaments of fiberglass from the glass composition in a conventional viscous melt spinning fiberglass forming process as disclosed in K. L. Lowenstein, The Manufacturing Technology of Continuous Glass Fibers, Third Edition, Elsevier Science Publishing Company, Inc. (1993). The filaments of fiberglass preferably have diameters of about four microns to five hundred microns, more preferably about ten microns to thirty microns. The filaments of fiberglass may be leached by exposing the fiberglass to an acid such as sulfuric acid or hydrochloric acid at an elevated temperature such as about 80° C. Alternatively, the fiberglass filaments may be leached by reacting the fiberglass with a base such as sodium hydroxide or potassium hydroxide. Preferably, the filaments of fiberglass are passed directly from the extrusion device into an acid bath. The step of leaching the filaments of fiberglass with an acid is believed to cause metal ions present in the fiberglass to leach out of the fiberglass thereby creating the pores 22. The base used in the step of reactive leaching the fiberglass filaments is believed to chemically attack the silicon oxide portion of the fiberglass to produce the pores. By either route, this leaching process weakens the glass composition and typically affects only the surface of the fiberglass filaments. The porous fiberglass filaments are ground to produce the fiberglass particles 16 having lengths of about twenty microns to one half inch. For use on a sent, the particles are preferably twenty microns to fifty microns long. The grinding step causes the filaments to break and form the jagged, conchoidally shaped ends 30. Finally, the chemical composition 24 is mixed with the ground fiberglass particles. The chemical composition 24 may be aqueous or water soluble or may be an organic composition or soluble in an organic solvent. The ground fiberglass particles and the chemical composition may be mixed together in a stirred tank reactor to allow the chemical composition 24 to enter the pores 22 of the fiberglass particles 16. Because of the ink bottle shape of the pores 22, the chemical composition 24 readily enters the pores 22 but does not readily escape the pores 22 until the particles 16 dissolve.

The hollow fiberglass particles 16' may be prepared in a similar process. A water soluble glass composition is drawn through an annulus to form hollow filaments of fiberglass. The hollow fiberglass filaments are ground to produce ground hollow fiberglass particles 16'. The particles 16' have outside diameters and lengths similar to the particles 16. The particles 16' are likewise mixed with the chemical composition 24. The cores 32 of the hollow fiberglass particles 16 readily become filled with the chemical composition 24 via capillary action.

The fiberglass particles 16 or 16' may be used as a chemical delivery system. In particular, the fiberglass particles 16 or 16' may be used as an intravascular drug delivery device.

The vascular drug delivery device 10 is prepared by coating an exterior surface of the sent 14 with a layer 18 of a biocompatible adhesive. In the coating step, the sent 14 may be dipped into, rolled into or brushed with the biocompatible adhesive. The adhesive coated sent 14 may likewise be dipped into, rolled into, dusted with or brushed with the fiberglass particles 16. Other techniques may also be employed to coat the exterior surface of the sent 14 with the biocompatible adhesive layer 18 and to contact the adhesive layer 18 with the fiberglass particles 16. The fiberglass particles 16 adhere to the adhesive layer 18 with at least a portion of the jagged, conchoidally shaped ends 30 being free and extending away from the sent 14.

Although the present invention has been described with respect to ground fiberglass particles containing a chemical composition, such as a drug, which are supported on a sent, such particles may be delivered unsupported orally or parenterally such as intravenously or intramuscularly. Water soluble glass is inert and ultimately is dissolved in bodily fluids. Hence, a composition including water soluble fiberglass particles containing a drug provides a safe and effective method of sustained released drug delivery.

Furthermore, the water soluble fiberglass particles may be used to release over time a wide variety of substances other than a drug composition such as plant treatment substances including fertilizers and biocides such as pesticides, insecticides and the like. The water soluble fiberglass particles may be filled with a plant treatment substance and dispersed into soil surrounding vegetation or sprayed onto a plant. Ground water, moisture or rain water which contacts the particles containing a plant treatment substance will dissolve the particles over time thereby releasing the substance.

The water soluble fiberglass particles may also be used as a dissolvable catalyst support. The pores 22 of the fiberglass particles 16 or the hollow cores 32 of the fiberglass particles 16' may be filled with a catalyst composition. The particles 16 or 16' containing the catalyst composition may be used in a stirred tank reactor or fluidized bed or other reactor containing aqueous reactants. The particles 16 or 16' will release the catalyst composition and eventually completely dissolve in the reactants, thus obviating the need to filter the reaction mixture to remove a catalyst support therefrom. By controlling the solubility of the fiberglass of the particles 16 or 16', the rate at which the catalyst composition is released into the reaction mixture may be controlled, thus providing controlled chemical reaction engineering of the reaction mixture.

Similarly, the pores 22 or hollow core 32 of the respective particles 16 or 16' may be filled with a first chemical reactant. The particles 16 or 16' containing the first chemical reactant may be mixed into a reactor containing an aqueous second chemical reactant. As the particles 16 or 16' dissolve, the first chemical reactant is released into the second chemical reactant and reacts therewith. The solubility of the particles 16 or 16' determines the rate at which the first chemical reactant is released into the reaction mixture, thus allowing for control of the reaction process.

A curing agent for polymers such as elastomers or cement or the like may also be contained within the water soluble fiberglass particles 16 or 16'. As the fiberglass particles 16 or 16' dissolve over time, the curing agent is -released in a controlled manner to allow slow curing of the product.

The chemical delivery system has been disclosed herein as using particles formed from water soluble fiberglass. However, the invention further includes other particles, which may be porous or hollow, formed from other materials such as certain plastics or polymers including polypropylene or polyesters. Porous or hollow particles made from these alternative materials may be soluble in certain organic compositions instead of water and used in organic chemical processes.

Although the present invention has been described in detail to the discussed embodiments, various modifications may be made by one of ordinary skill in the art without departing from the spirit and scope of the present invention. Therefore, the scope of the present invention should be determined by the attached claims.

I claim:

1. A carrier composition for release of a substance, said carrier composition comprising a plurality of water soluble glass fibers having diameters of about four microns to about five hundred microns and lengths of about twenty microns to one half inch, wherein said fibers are adapted to releasably contain a substance such that the substance is released from said fibers as said fibers are dissolved in water.

2. The carrier composition of claim 1 wherein said glass fibers each define a hollow core and wherein said fibers are adapted to releasably contain the substance within said hollow core.

3. The carrier composition of claim 1 wherein said glass fibers each define at least one pore and wherein said fibers are adapted to releasably contain the substance within said pores.

4. A sustained release substance delivery device comprising:
   a plurality of water soluble glass fibers having diameters of about four microns to about five hundred microns, said glass fibers each defining a hollow core; and
   a substance releasably contained within said hollow core of said glass fibers, wherein said glass fibers dissolve when contacted with water such that said substance is released from within said hollow cores of said glass fibers.

5. The device of claim 4 wherein said substance is selected from the group consisting of a drug, a fertilizer, a biocide, a chemical reactant and a catalyst.

6. The device of claim 5 wherein said substance is a gene.

7. A sustained release gene delivery device comprising:
   a plurality of water soluble glass fibers having diameters of about four microns to about five hundred microns; and
   a gene releasably contained within said glass fibers, wherein said glass fibers dissolve when contacted with water such that said gene is released from within said glass fibers.

8. A carrier composition for release of a substance, said carrier composition comprising a plurality of water soluble glass fibers, wherein said glass fibers each define a hollow core and further wherein said fibers are adapted to releasably contain a substance within said hollow core such that said substance is released from within said hollow cores as said fibers are dissolved in water.

9. The carrier composition of claim 8 wherein said glass fibers have lengths of about twenty microns to one half inch.

10. The carrier composition of claim 8 wherein said glass fibers have diameters of about four microns to about five hundred microns.

11. A carrier composition for release of a substance, said carrier composition comprising a plurality of water soluble glass fibers, wherein said glass fibers each define at least one pore and further wherein said fibers are adapted to releasably contain a substance within said at least one pore such that said substance is released from within said pores as said fibers are dissolved in water.

12. The carrier composition of claim 11 wherein said glass fibers have diameters of about four microns to about five hundred microns.

13. The carrier composition of claim 11 wherein said glass fibers have lengths of about twenty microns to one half inch.

14. A sustained release substance delivery device comprising:
   a plurality of water soluble glass fibers having diameters of about four microns to about five hundred microns, wherein said glass fibers define a plurality of pores; and
   a substance releasably contained within said pores of said glass fibers, wherein said glass fibers dissolve when contacted with water such that said substance is released from within said pores of said glass fibers.

15. The device of claim 14 wherein said substance is selected from the group consisting of a drug, a fertilizer, a biocide, a chemical reactant and a catalyst.

16. A method of preparing a fiberglass carrier composition comprising the steps of:
   providing a water soluble glass composition;
   forming fibers of water soluble glass from said glass composition;
   creating pores in said fibers to produce porous water soluble fiberglass;
   grinding said porous water soluble fiberglass to produce ground porous water soluble fiberglass particles; and
   mixing a substance with said ground porous water soluble fiberglass such that said substance enters said pores.

17. The method of claim 16 wherein said step of creating pores in said fibers comprises leaching said fibers with an acid.

18. A method of preparing a fiberglass carrier composition comprising the steps of:
   providing a water soluble glass composition;
   forming hollow fibers of water soluble glass from said glass composition such that said hollow fibers each define a hollow core;
   grinding said hollow water soluble fiberglass to produce ground hollow water soluble fiberglass particles; and
   mixing a substance with said ground hollow water soluble fiberglass such that said substance enters said hollow cores of said hollow fibers.

* * * * *